US006765983B2

(12) United States Patent
Yan et al.

(10) Patent No.: US 6,765,983 B2
(45) Date of Patent: Jul. 20, 2004

(54) METHOD AND APPARATUS FOR IMAGING A REGION OF DYNAMIC TISSUE

(75) Inventors: Weizhong Yan, Clifton Park, NY (US);
Peter Michael Edic, Albany, NY (US);
Maria Iatrou, Clifton Park, NY (US);
Kai Frank Goebel, Balston Lake, NY (US); Erdogan Cesmeli, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/318,909

(22) Filed: Dec. 13, 2002

(65) Prior Publication Data

US 2004/0114727 A1 Jun. 17, 2004

(51) Int. Cl.[7] .................................................. A61B 6/03
(52) U.S. Cl. .......................................... 378/8; 378/901
(58) Field of Search ........................... 378/4, 8, 15, 901

(56) References Cited

U.S. PATENT DOCUMENTS 5,383,231 A * 1/1995 Yamagishi .................... 378/15

2002/0025017 A1 * 2/2002 Stergiopoulos et al. ........ 378/8
2002/0034276 A1 * 3/2002 Hu et al. ......................... 378/8

* cited by examiner

Primary Examiner—David V Bruce
(74) Attorney, Agent, or Firm—Fletcher Yoder, P.C.

(57) ABSTRACT

A technique is provided for reducing motion-related artifacts present in CT images attributable to the dynamic nature of the imaged tissue or the time-varying concentration of a contrast agent. A region of interest that encompasses a structure of diagnostic significance is selected. For projections acquired by the various rows of detectors in a multi-slice CT imaging system, the portions of the projections attributable to the projection of the region of interest are averaged for each view angle. The projections containing these averaged values are then combined with the projections which do not encompass the region of interest. The combined projection set may be reconstructed to form a CT image of the dynamic tissue. In addition, a smoothing step may be performed to interpolate projection values around the region of interest to smooth the visual transition to the unaveraged portions of the image.

28 Claims, 4 Drawing Sheets

METHOD AND APPARATUS FOR IMAGING A REGION OF DYNAMIC TISSUE

BACKGROUND OF THE INVENTION

The present invention relates generally to the field of medical imaging and more specifically to the field of cardiac imaging by computed tomography. In particular, the present invention relates to the correction of motion artifacts, such as due to cardiac motion and to concentration variations of a contrast agent over time.

Computed tomography (CT) imaging systems measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced projection images. It should be pointed out that a CT system produces data that represents the distribution of linear attenuation coefficients of the scanned object. This data is then reconstructed to produce an image, which is typically displayed on a cathode ray tube, and may be printed or reproduced on film. A virtual 3-D image may also be produced by a CT examination.

CT scanners operate by projecting fan shaped or cone shaped X-ray beams from an X-ray source that is collimated and passes through the object, such as a patient, that is then detected by a set of detector elements. The detector element produces a signal resulting from the attenuation of the X-ray beams, and the data are processed to produce signals that represent the line integrals of the attenuation coefficients of the object along the ray paths. A collection of these signals at a particular view angle is typically called a projection. By using reconstruction techniques, such as filtered back-projection, useful images are formulated from the projections. The locations of pathologies may then be located either automatically, such as by a computer assisted detection (CAD) algorithm or, more conventionally, by a trained radiologist. CT scanning provides certain advantages over other types of techniques in diagnosing disease particularly because it illustrates the accurate anatomical information about the body. Further, CT scans may help doctors distinguish between types of abnormalities more accurately.

CT imaging, when performed for moving structures such as the heart, has proven problematic due to the dynamic nature of the tissue, and it is only with the advent of faster CT scanners and multi-slice systems that imaging of certain types of structures, such as the heart in cardiac CT imaging, has proven feasible. However, even with these improved systems, the motion can produce image artifacts, such as streaking artifacts, which mask the anatomical structure. This type of image artifact may also be produced by the temporal variations in concentration of the contrast agents employed to enhance image acquisition, as of the cardiac chambers and vessels.

In particular, certain image artifacts, such as the streaking artifact, occur due to projection measurement inconsistency during image acquisition, such as resulting from cardiac motion or the time-varying concentration of the contrast agent In the case of cardiac motion, the change in shape of the scanned object results in projection measurement inconsistency. Similarly, the time-varying concentration of the contrast agent produces projection measurement inconsistency due to variations in the attenuation coefficients which result. Either or both of these effects is sufficient to produce image artifacts, such as rays or streaks which may obscure a clinically significant feature, such as a plaque or lesions. These image artifacts also reduce the diagnostic value of the CT images by failing to highlight areas of interest in which a contrast agent should flow.

Motion artifacts are typically addressed in CT imaging by either patient restraint to prevent motion, or by gating techniques. Patient restraint is obviously not effective in the case of cardiac CT imaging. Gating techniques operate by reconstructing the acquired images at the same point in a motion cycle, such as the cardiac cycle, thus minimizing motion artifacts in the reconstructed images. While gating is helpful in reducing motion artifacts, it requires a longer scan time because the technique employs only a subset of the acquired data for retrospective gating schemes. The longer scan time in turn requires increased amounts of breath holding and increased amounts of contrast agent. In addition, gating does not reduce artifacts related to time-varying concentrations of contrast agent and may even exacerbate this problem due to the reliance upon temporally staggered data sets.

Other methods of addressing motion, such as cardiac motion, include using two X-ray sources to obtain two sets of projection data identical in space but separated in time. The difference between the two sets of projection data allows the moving heart to be isolated and motion to be identified. This technique, however, requires hardware modification of the CT scanning system and does not reduce artifacts related to time-varying concentration of contrast agent.

Methods of reducing the artifacts caused by the time-varying concentration of the contrast agent, but not cardiac motion, also exist. For instance, methods of projection interpolation have been proposed which are simple to implement but have only limited effectiveness in reducing the image artifacts. Other methods have been proposed which involve multiple computational steps, allowing errors to accumulate throughout the calculations. These accumulated errors may themselves distort the final image.

As noted, the existing techniques generally fail to address the potential causes of image artifacts, such as streaking artifacts. Likewise, many of the techniques are either largely ineffective at artifact reduction in general or themselves distort the final image. An effective method of reducing such image artifacts, while maintaining or improving the clinical diagnostic value of the final image, is therefore needed.

BRIEF DESCRIPTION OF THE INVENTION

The present technique provides a novel technique to minimize or eliminate motion-related artifacts produced when imaging dynamic tissue, such as cardiac tissue. Particularly, the technique provides for a method and system for averaging projection values corresponding to the projection of a region of interest in the object at each view angle. The technique thereby allows motion related artifacts, such as streaking, to be minimized or eliminated.

In accordance with one aspect of the technique, a method is provided for imaging a dynamic region of interest using a multi-row CT imaging system. The technique provides for segmenting a region of interest. Two or more successive projections from a projection data set are selected. Each of the two or more successive projections is acquired at the same view angle and axial position, and a portion of data corresponding to a projection of the region of interest upon a detector is identified. The portion of data of each of the two or more successive projections is averaged to produce an averaged portion. The portion of data of each of the two or more successive projections is replaced with the averaged portion to create two or more respective averaged projections. The two or more averaged projections are combined with the remainder of the projection data set to produce a formatted data set. An image is reconstructed from the formatted data set.

In accordance with a further aspect of the technique, a CT cardiac image analysis system is provided which includes a computer system capable of being operably coupled to at least one of a CT cardiac image acquisition system or CT image storage system. The computer system is configured to segment a region of interest. In addition, the computer system is configured to select two or more successive projections from a projection data set. Each of the two or more successive projections are acquired at the same view angle and axial position and a portion of data corresponding to a projection of the region of interest upon a detector is identified. The computer system is also configured to average the portion of data of each of the two or more successive projections to produce an averaged portion and to replace the portion of data of each of the two or more successive projections with the averaged portion to create two or more respective averaged projections. The computer system is also configured to combine the two or more averaged projections with the remainder of the projection data set to produce a formatted data set and to reconstruct an image from the formatted data set. The image analysis system also includes an operator workstation operably coupled to the computer system configured to display the image.

In accordance with another aspect of the technique, a CT cardiac image analysis system is provided. The CT cardiac imaging system includes a means for acquiring a set of CT projection images. The CT cardiac imaging system also includes a means processing the set of CT image projections such that motion artifacts are minimized in a reconstructed image.

In accordance with a further aspect of the technique, a tangible medium is provided which includes a routine for segmenting a region of interest. The tangible medium also includes a routine for selecting two or more successive projections from a projection data set. Each of the two or more successive projections is acquired at the same view angle and axial position, and a portion of data corresponding to a projection of the region of interest upon a detector is identified. In addition, the tangible medium includes a routine for averaging the portion of data of each of the two or more successive projections to produce an averaged portion. A routine is also included for replacing the portion of data of each of the two or more successive projections with the averaged portion to create two or more respective averaged projections and for combining the two or more averaged projections with the remainder of the projection data set to produce a formatted data set A routine is included for reconstructing an image from the formatted data set.

DETAILED DESCRIPTION OF SPECIFIC EMBODIMENTS

Figure 1:
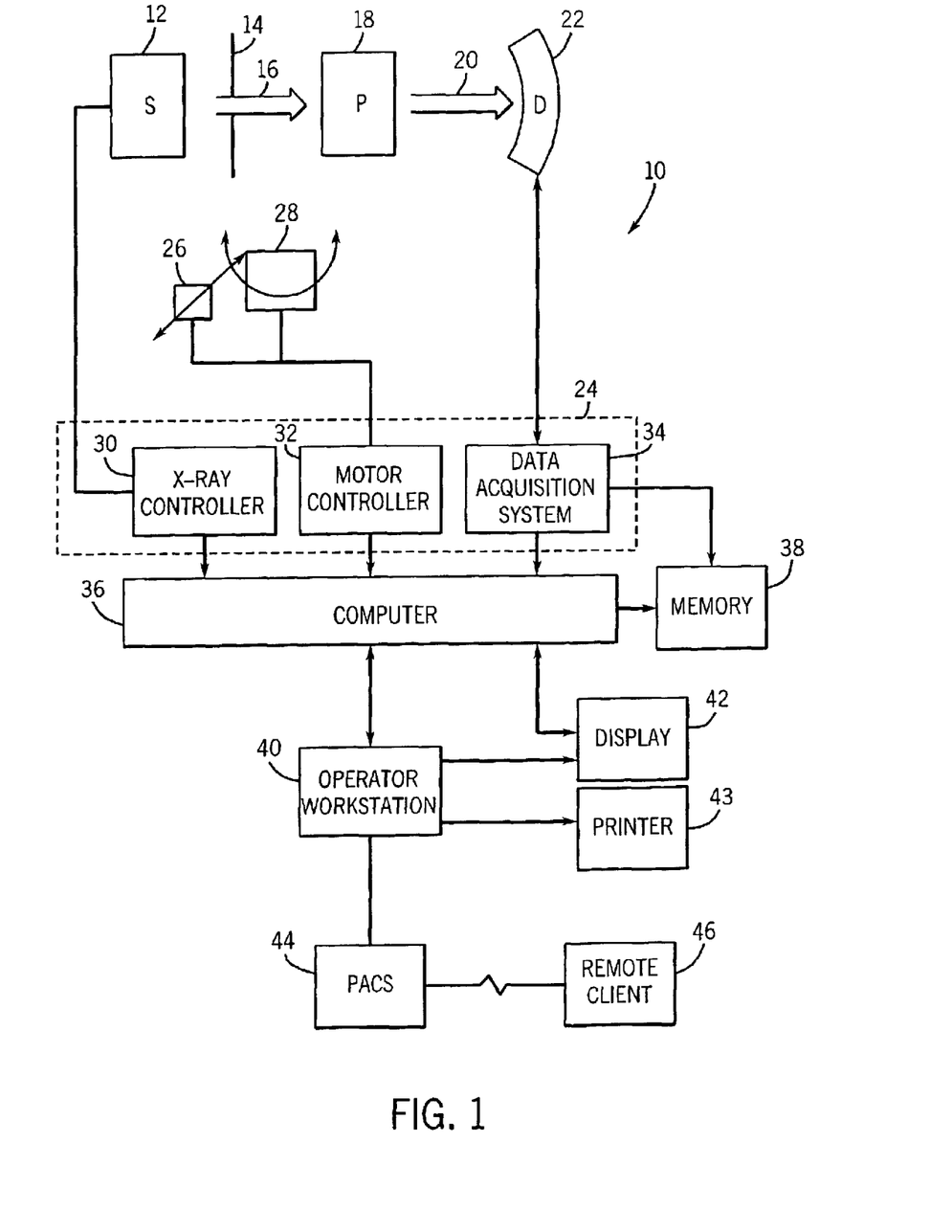
FIG. 1 is a diagrammatical view of an exemplary imaging system in the form of a CT imaging system for use in producing processed images in accordance with aspects of the present technique.

FIG. 1 illustrates diagrammatically an imaging system 10 for acquiring and processing image data. In the illustrated embodiment, system 10 is a computed tomography (CT) system designed both to acquire original image data, and to process the image data for display and analysis in accordance with the present technique. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject. In a typical multi-row detector array 22, there are 4, 8, or 16 rows of detector elements each comprising multiple detector elements.

Source 12 is controlled by a system controller 24, which furnishes both power and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 and moreover, to a memory 38. It should be understood that any type of memory to store a large amount of data might be utilized by such an exemplary system 10. Also the computer 36 is configured to receive commands and scanning parameters from an operator via an operator workstation 40 typically equipped with a keyboard and other input devices. An operator may control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image and to control imaging. Further, the operator workstation 40 may also be coupled to a picture archiving and communications system (PACS) 44 or a printer 43. It should be noted that PACS 44 might be coupled to a remote system 46, radiology department information system (RIS), hospital information system (HIS) or to an internal or external network, so that others at different locations may gain access to the image and to the image data.

It should be further noted that the computer 36 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
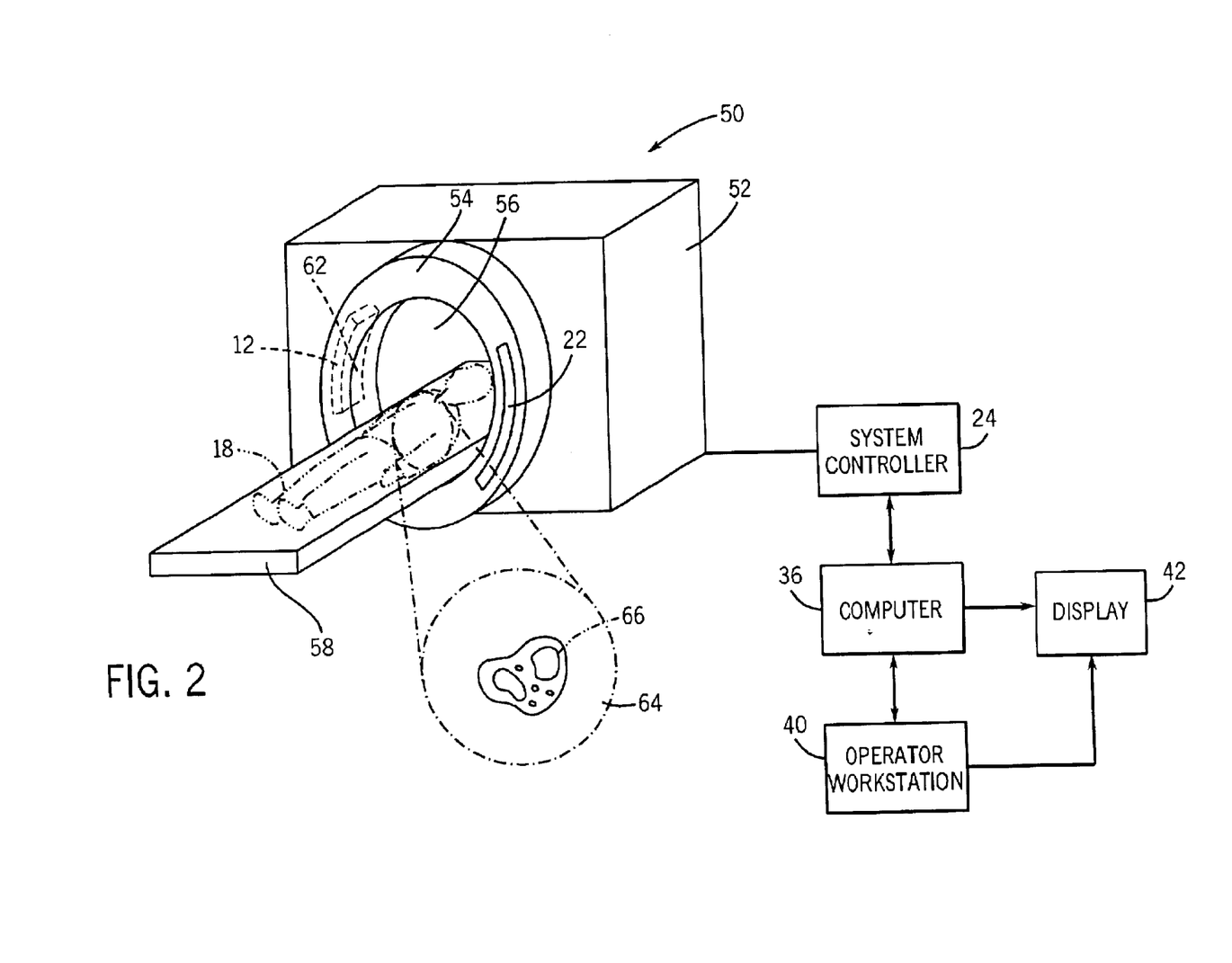
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is typically a multi-slice detector CT (MCT) which offers a wide array of axial coverage, high gantry rotational speed, and high spatial resolution, all of which allow the use of sophisticated reconstruction algorithms, such as for cardiac imaging. The CT scanning system 50 is illustrated with a frame 52, and a gantry 54 that has an aperture 56. The aperture 56 may typically be 50 cm in diameter. Further, a patient table 58 is illustrated positioned in the aperture 56 of the frame 52 and the gantry 54. The patient table 58 is adapted so that a patient 18 may recline comfortably during the examination process. Additionally, the patient table 58 is configured to be displaced linearly by the linear positioning subsystem 26 (see FIG. 1). The gantry 54 is illustrated with the source of radiation 12, typically an X-ray tube that emits X-ray radiation from a focal point 62. For imaging, the stream of radiation is directed towards a region of interest that includes an anatomy to be imaged, such as the heart of the patient 18.

In typical operation, X-ray source 12 projects an X-ray beam from the focal point 62 and toward detector array 22.

The detector 22 is generally formed by a plurality of detector elements, which sense the X-rays that pass through and around a subject of interest, such as the heart. Each detector element produces an electrical signal that represents the intensity of the X-ray beam at the position of the element during the time the beam strikes the detector. Furthermore, the gantry 54 is rotated around the subject of interest so that a plurality of radiographic views may be collected by the computer 36. Thus, an image or slice is acquired which may incorporate, in certain modes, less or more than 360 degrees of projection data, to formulate an image. The image is collimated to a desired thickness, typically between 0.5 mm and 10 mm using either lead or tungsten shutters in front of the X-ray source 12 and different detector apertures 22. The collimator 14 (see FIG. 1) typically defines the size and shape of the X-ray beam that emerges from the X-ray source 12.

Thus, as the X-ray source 12 and the detector 22 rotate, the detector 22 collects data of the attenuated X-ray beams. Data collected from the detector 22 then undergoes pre-processing and calibration to condition the data to represent the line integrals of the attenuation coefficients of the scanned objects. The processed data, commonly called projections, are then filtered and back-projected to formulate an image of the scanned area. As mentioned above, the computer 36 is typically used to control the entire CT system 10. The main computer that controls the operation of the system may be adapted to control features enabled by the system controller 24. Further, the operator workstation 40 is coupled to the computer 36 as well as to a display, so that the reconstructed image may be viewed.

As will be appreciated by those skilled in the art, the CT system acquires data continuously, at discrete image view frames corresponding to specific angular positions, as the source and detector rotate about the subject. Moreover, in helical modes of operation, the data are collected as the subject is displaced by movement of the table. The resulting data set contains a large quantity of data points generally indicative of the intensity of radiation received by the detector elements at each of the angular positions. Reconstruction of images, then, proceeds by selecting desired "reconstruction windows" or spans of data points which, based upon the reconstruction algorithm employed, provides sufficient information to calculate locations of features causing X-ray attenuation. Such reconstruction techniques may employ windows spanning 360° of angular positions, but for reasons of computational efficiency, generally rely upon windows spanning 180° plus the included angle of the X-ray beam (typically referred to as "α"). Due to redundancy in the projection data acquired for a window spanning 360° of angular positions, windows spanning 180° plus α generally suffice for image reconstruction. Other techniques may employ a plurality of shorter windows, such as in techniques referred to as multi-sector reconstruction.

Once reconstructed, a cardiac image produced by the system of FIGS. 1 and 2 reveals the heart of the patient 18. As illustrated generally in FIG. 2, the image 64 may be displayed to show patient features, such as indicated at reference numeral 66 in FIG. 2. In traditional approaches to diagnosis of medical conditions, such as disease states, and more generally of medical events, a radiologist or physician would consider the reconstructed image 64 to discern characteristic features of interest. Such features 66 might include the major blood vessels, such as the superior vena cava, coronary blood vessels, plaques within such vessels, and other features, which would be discernable in the image based upon the skill and knowledge of the individual practitioner. Other analyses may be based upon capabilities of various CAD algorithms.

In CT imaging of moving anatomies, such as cardiac imaging, one problem that occurs, due to the dynamic nature of the tissue, is the presence of streaking or other motion related artifacts within the final image. While the present technique is particularly well suited to cardiac imaging, and will be described in that context, it should be borne in mind that the technique may also be applied to imaging other anatomies where similar problems are encountered. These artifacts may result from the movement of the tissue itself, the swirling motion of an unevenly distributed contrast agent entering and exiting the cardiac chambers, or the time-varying concentration of the contrast agent during the imaging process.

Patient restraint (e.g. breath holding), one of the traditional methods of addressing motion artifacts during CT imaging, is not applicable to cardiac imaging because of the involuntary nature of cardiac motion. Gating, that is, processing the collected projection data in conjunction with an ECG signal, may be employed to selectively process the projection data to minimize motion artifacts. Gating techniques, however, require longer scan times and possibly a greater use of contrast agents. Attempts have also been made to reduce the swirling effects of the contrast agent by performing the scan more quickly or by judicious administration of the contrast agent. These techniques however have not eliminated the presence of motion-related artifacts, such as streaking, from cardiac CT images.

The present technique is useful in multi-row detector systems, i.e., multi-slice CT systems, for reducing or eliminating such motion-related artifacts. In such a system, projection data for a location is sampled multiple times by the different detector rows. Ignoring the small cone angle difference between the multiple detector rows, the projections obtained by the multiple rows are of the same cardiac location but scanned at different times and may therefore be at different cardiac phases. Though the projections obtained by the multiple detector rows correspond to different cardiac phases, the location of a region of interest, such as the superior vena cava (SVC), on reconstructed images does not substantially fluctuate from image to image. In accordance with the present technique, the relative consistency of the location of such a region of interest allows the averaging of a portion of the projection data which corresponds to the projection data attributable to the region of interest. That is, in successive projections obtained at the same rotational angle and general linear displacement, a similar portion of the resulting projection data, i.e., the data detected by the equivalent detector elements in different detector rows at different times, is produced by X-rays passing through the region of interest. In other words, the projection of the region of interest upon the detector at a certain rotational angle is essentially constant as the scan is performed, allowing the projections attributable to the region of interest to be averaged for each rotational angle to minimize or eliminate motion-related artifacts otherwise present in cardiac CT imaging.

Figure 3:
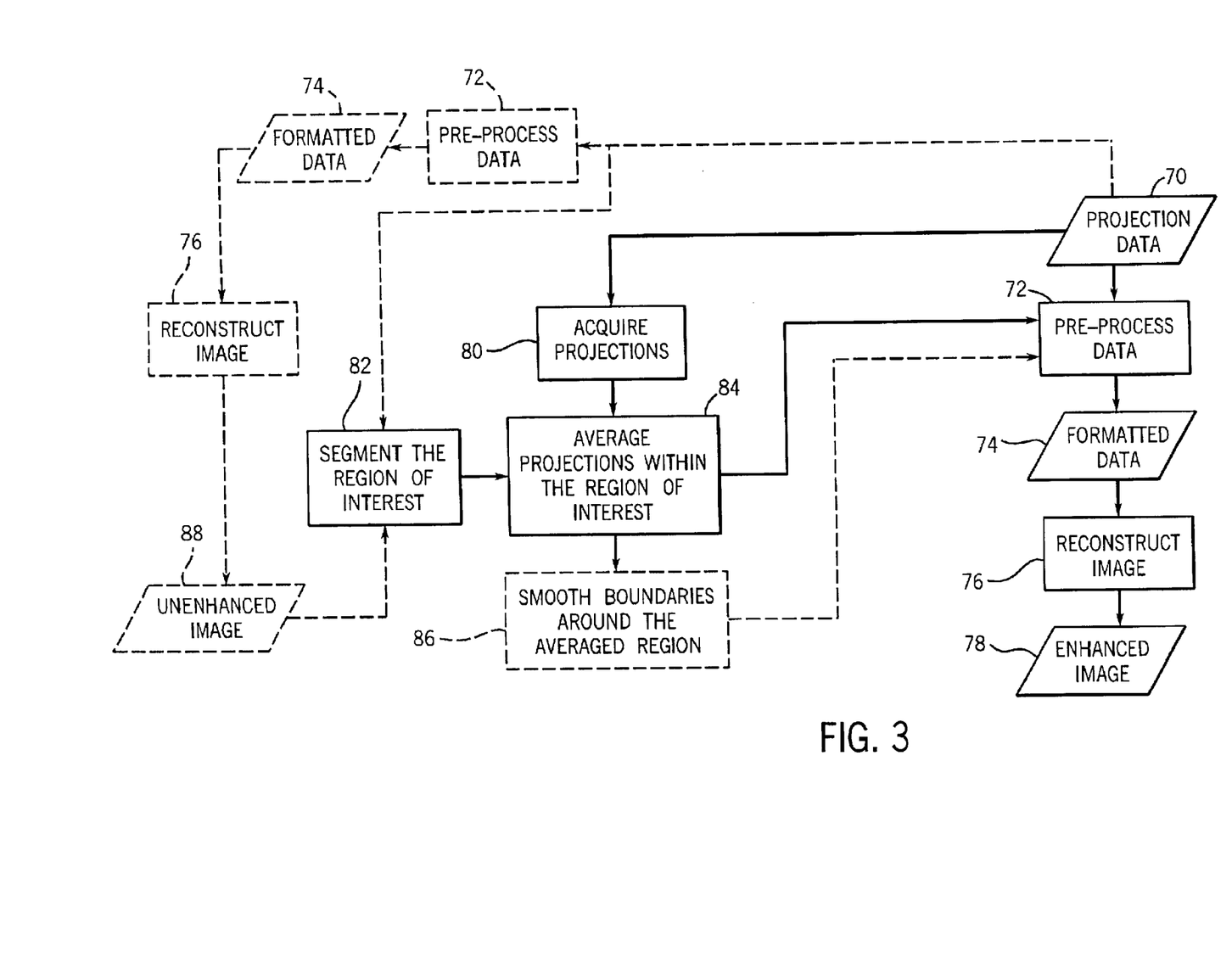
FIG. 3 is a flowchart depicting the present technique of averaging projection data corresponding to a region of interest during CT imaging.

An example of this technique is depicted in FIG. 3. Initially, raw projection data 70 is collected, such that data corresponding to either 360 degrees of data or to 180 degrees plus the fan angle (180°+α) can be used for image reconstruction as discussed above. The procedure for generating an image from raw projection data 70 typically begins by pre-processing the data, as depicted at block 72. Pre-processing the data 72 typically includes reading in the raw projection data 70 along with other imaging information, such as the corresponding view frame and Z-location, i.e. the rotational and axial locations associated with each projection. Various weighting schemes, such as Z-interpolation and view weighting, may also be applied to the raw projection data 70 at this pre-processing stage 72 in order to facilitate reconstruction of raw projection data 70. The output of this pre-processing stage 72 is a formatted data set 74. The formatted data set 74 may then be used for image reconstruction, as depicted at block 76, to form the final cardiac image 78.

The present technique contributes to the step of pre-processing the data, as depicted at step 72, and thereby enhances the formatted data 74 that undergoes reconstruction, as depicted at step 76, such that motion-related artifacts are reduced or eliminated. In particular, the present technique acquires projections, as depicted at step 80, from the set of projection data 70. The acquired projections are acquired at the same view angle and include data corresponding to a region of interest. In addition, the present technique segments the region of interest, as depicted at step 82, within a reconstructed image 88 of the object. The portion of each projection of the projection data set 70 which corresponds to the projection of the region of interest upon the detector 22 is identified and averaged, as depicted at step 84 for the set of acquired projections. The set of acquired projections for which these portions are averaged may then be provided to the pre-processing step 72 and are thereby incorporated into the formatted data set 74 for reconstruction 76. In addition, a boundary smoothing step 86 may be present which interpolates projection values within each acquired projection in a zone around the portion attributable to the projection of the region of interest upon the detector to smooth the transition within the enhanced image 78 around the region of interest. The boundary smoothing step 86 provides the interpolated values for the acquired set of projections to the pre-processing step 72 as well for incorporation into the formatted data set 74.

Figure 4:
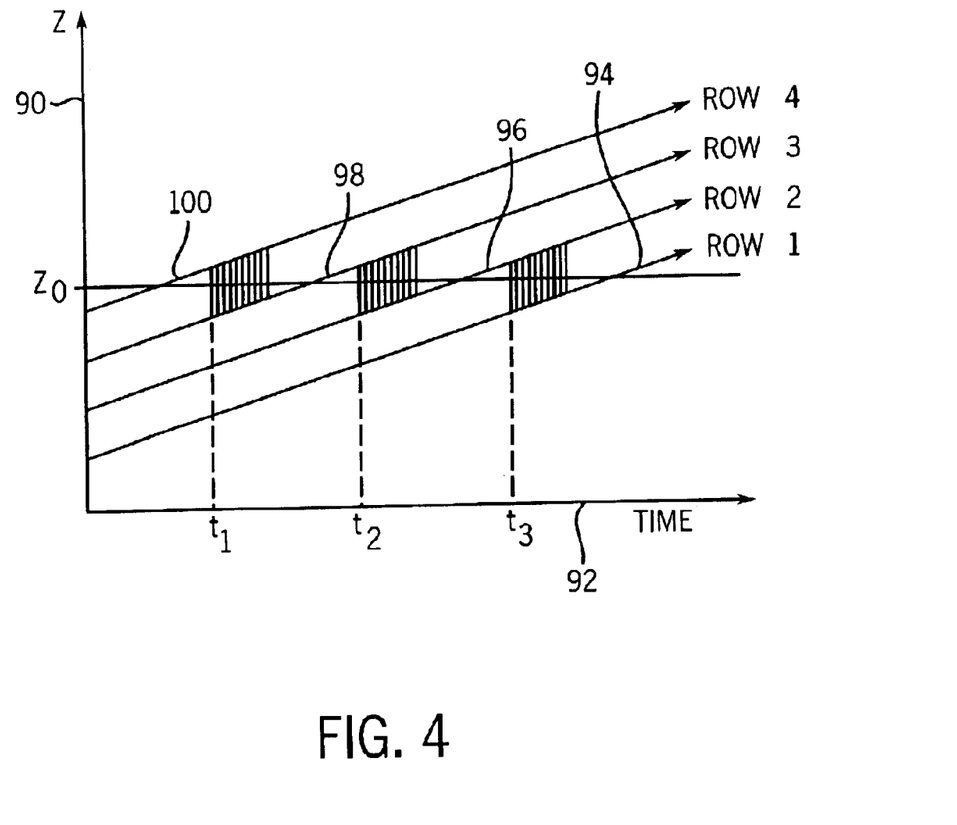
FIG. 4 is a chart depicting the relationship between linear displacement and time in a CT imaging system.

A typical implementation of the step 80 of acquiring projections is illustrated in FIG. 4. In FIG. 4, the typical Z-position versus time is illustrated diagrammatically by depicting the linear position (Z) over time (t) such that the linear, Z, position is represented along the vertical axis 90 and time is represented along the horizontal axis 92. Trace 94 depicts the relationship between linear position, Z, and time of a first detector row. Similarly, traces 96, 98, and 100 depict the same relationship respectively for second, third, and fourth detector rows. Within the depicted Z-t space, for any given linear position, such as $Z_0$, and any given view angle, or equivalently, time, the view number for each of the projection sets at that linear position can be determined. The number of projection sets to be processed depends on the pitch value of the scanner, for example, at a pitch of 1, the number of projection sets equals 3. Based upon the linear position and the determined view number, the desired projection sets encompassing the region of interest can be extracted at step 80 from the projection data set 70 (see FIG. 3) or from the pre-processed data 72.

To aid in the acquisition of the necessary projections in step 80, a region of interest in the reconstructed image 88 of the object is segmented, as depicted at step 82 of FIG. 3, such that any particular structures of interest, such as the SVC, are within the segmented region. In one embodiment, the raw projection data 70 is pre-processed at step 72 to provide formatted data 74. The formatted data 74 is reconstructed at step 76 to form an unenhanced image 88. The unenhanced image 88 may be manually or automatically analyzed to locate the region to be segmented at step 82.

Automatic analysis may be by means of a threshold-based or other segmentation algorithm. To simplify implementation, the segmented region is typically a circle sized to encompass the desired structure so that the exact shape and location of the structure does not need to be known specifically within each projection set. The size of the circle employed may be determined empirically. The centroid of the selected region is then determined and used as the center of the circle defining the region of interest within the image 76. In an alternative embodiment, the region of interest may be identified and segmented at step 82 within the projection data 70 by various means, including the use of automated segmentation algorithms employing threshold based or other types of comparisons.

Once the region of interest has been segmented at step 82 and the desired projection sets have been acquired at step 80, the portion of each acquired projection corresponding to the projection of the region of interest upon the detector 22 can be averaged 84. The averaging, thereby, occurs over each successive rotation within the projection of the region of interest. The averaging is performed on a detector element-by-detector element and view frame-by-view frame basis, with view frames from the same angular positions being employed. Within each view frame (i.e. angular position) in the reconstruction window, signals from corresponding detector elements, or interpolated values if appropriate, in the acquired projections are averaged, such that the portion of the projection data corresponding to the region of interest in the acquired projections is averaged over time. It should be noted that the number of elements averaged for the region of interest may, and typically will, vary for different view frames due to the varying width of the projection of the region of interest on the detector array at different angular positions around the subject.

The $i^{th}$ projection set which is acquired at the view angle, $\beta$, by the detector number $\gamma$ may be represented as $P_1(\beta,\gamma)$. Mathematically, therefore, the averaged projection, $P(\beta,\gamma)$, can be expressed as:

$$P(\beta, \gamma) = \begin{cases} \frac{1}{n}\sum_{i=1}^{n} P_i(\beta, \gamma) & \text{For } \gamma \in \lfloor \gamma_1^\beta, \gamma_2^\beta \rfloor \\ P_j(\beta, \gamma) & \text{For } \begin{array}{l} \lambda \notin \lfloor \gamma_1^\beta, \gamma_2^\beta \rfloor \\ j \in \lfloor 0, 1, 2, \ldots, n-1 \rfloor \end{array} \end{cases}$$

where n is the number of projection sets used for averaging, and $\gamma_1^\beta$ and $\gamma_2^\beta$ are the minimum and maximum detectors numbers which define the projection of the region of interest at the view angle $\beta$.

In this manner, the portion of each acquired projection subset attributable to the projection of the region of interest on the detector 22 is averaged at each view angle position for successive interpolated row data at the same linear displacement, or Z-location. In a typical multi-slice CT system, three or fewer interpolated data sets are averaged for the region of interest. In a typical multi-slice CT system, 360° of projections are acquired but only 180°+α of the acquired projections are processed and reconstructed, as the remainder of the data represents redundant information as discussed above.

In certain cases however, such as where the imaged anatomy does not undergo excessive displacement, more of the acquired projections may be used to add additional averaging points to the data and thereby improve consistency. In particular, where desired, the acquired projections may be utilized from a first reconstruction window on one side of the subject and from alternate measurements acquired at conjugate view angle positions not used for image reconstruction. By using these redundant projections, twice as many data points are available for averaging.

Returning to FIG. 3, once the portion of the acquired projections attributable to the region of interest is averaged at step 84, the acquired projections incorporating the averaged portions are contributed to the pre-processing step 72 in place of the unaveraged counterparts to comprise a part of the formatted data set 74 which will be reconstructed. In particular, those projections encompassing a portion of the region of interest in the formatted data set 74 include averaged values for the portion of each projection attributable to the projection of the region of interest upon the detector 22.

Additionally, a transition zone around the projection of the region of interest may be processed to prevent or reduce a discontinuity at the boundary of the averaged and non-averaged regions in the reconstructed image 78, as depicted by boundary smoothing step 86 of FIG. 3. In one embodiment, a transition zone within each projection acquired at step 80 may be processed where the transition zone encompasses a zone on either side of the portion of the acquired projection attributable to the region of interest. The transition zone may be processed by averaging similar to that undergone by the portion of the projection attributable to the region of interest, as discussed above. For example, the transition zone may encompass the equivalent of ten detector elements on either side of the portion of the acquired projection attributable to the projection of the region of interest on the detector 22. The averaged projection values within the transition zone may then be smoothed by interpolating with measured, i.e., unaveraged, projection values. For example, a non-linear interpolation may be applied to the averaged projection values within this zone to obtain a smooth transition between the averaged projection data corresponding to that portion of the projection data attributable to the region of interest and to the remainder of the projection data. One such non-linear interpretation is defined by the relationship:

$$P(i) = P_1(i) \times \cos^2\left(\frac{\pi}{2} \cdot \frac{i}{N}\right) + \overline{P}(i) \times \sin^2\left(\frac{\pi}{2} \cdot \frac{i}{N}\right)$$

where P(i) is the final projection value at detector number i, $P_1(i)$ is the initial projection value at detector number i, $\overline{P}(i)$ is the averaged projection value at detector i in the transition region, and N is the width of the transition zone in number of detectors.

Subsequent to the averaging step 84 and the optional smoothing step 86, the resulting averaged and interpolated projections are reintegrated with the initial data at the pre-processing step 72 to form the formatted data set 74. This formatted data set 74 is then reconstructed at step 76 to form the enhanced image 78 in which motion artifacts are reduced and eliminated, thereby aiding analysis by a radiologist or subsequent automated processes such as via computer-assisted diagnosis (CAD).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for imaging a dynamic region of interest using a multi-row CT imaging system comprising:
   segmenting a region of interest;
   selecting two or more successive projections from a projection data set, wherein each of the two or more successive projections are acquired at the same view angle and axial position and comprise a portion of data corresponding to a projection of the region of interest upon a detector;
   averaging the portion of data of each of the two or more successive projections to produce an averaged portion;
   replacing the portion of data of each of the two or more successive projections with the averaged portion to create two or more respective averaged projections;
   combining the two or more averaged projections with the remainder of the projection data set to produce a formatted data set; and
   reconstructing an image from the formatted data set.

2. The method as recited in claim 1, wherein segmenting the region of interest comprises manually selecting the region of interest from a preliminary reconstructed image.

3. The method as recited in claim 1, wherein segmenting the region of interest comprises automatically selecting the region of interest from a preliminary reconstructed image.

4. The method as recited in claim 1, wherein segmenting the region of interest comprises automatically selecting the portion of data corresponding to the projection of the region of interest upon the detector from the processed data set.

5. The method as recited in claim 1, wherein segmenting the region of interest comprises automatically selecting the portion of data corresponding to the projection of the region of interest upon a detector from the projection data set.

6. The method as recited in claim 1, further comprising interpolating a boundary region of data corresponding to data on at least one side of the portion of data within each of the two or more respective averaged projections.

7. The method as recited in claim 6, wherein combining the two or more averaged projections with the remainder of the projection data set comprises weighting the remainder of the projection data set and the two or more averaged projections to compensate for redundancies.

8. The method as recited in claim 1, wherein combining the two or more averaged projections with the remainder of the projection data set comprises weighting the remainder of the projection data set and the two or more averaged projections to compensate for redundancies.

9. The method as recited in claim 1, further comprising forming the projection data set by selecting two or more raw projections corresponding to a prescribed cardiac phase from a raw data set.

10. A CT cardiac image analysis system comprising:
    a computer system capable of being operably coupled to at least one of a CT cardiac image acquisition system or a CT image storage system, the computer system configured to segment a region of interest; to select two or more successive projections from a projection data set, wherein each of the two or more successive projections are acquired at the same view angle and axial position and comprise a portion of data corresponding to a projection of the region of interest upon a detector; to average the portion of data of each of the two or more successive projections to produce an averaged portion; to replace the portion of data of each of the two or more successive projections with the averaged portion to create two or more respective averaged projections; to combine the two or more averaged projections with the remainder of the projection data set to produce a formatted data set; and to reconstruct an image from the formatted data set; and
    an operator workstation operably coupled to the computer system configured to display the image.

11. The CT cardiac image analysis system as recited in claim 10, wherein the computer system segments the region of interest based upon an operator input.

12. The CT cardiac image analysis system as recited in claim 10, wherein the computer system segments the region of interest based upon an automated algorithm.

13. The CT cardiac image analysis system as recited in claim 12, wherein the automated algorithm is a threshold analysis.

14. The CT cardiac image analysis system as recited in claim 10, wherein the computer system is further configured to interpolate a boundary region of data corresponding to data on at least one side of the portion of data within each of the two or more successive projections.

15. The CT cardiac image analysis system as recited in claim 14, wherein the computer system combines the two or more averaged projections with the remainder of the projection data set by weighting the remainder of the projection data set and the two or more averaged projections to compensate for redundancies.

16. The CT cardiac image analysis system as recited in claim 10, wherein the computer system combines the two or more averaged projections with the remainder of the projection data set by weighting the remainder of the projection data set and the two or more averaged projections to compensate for redundancies.

17. The CT cardiac image analysis system as recited in claim 10, wherein the computer system is further configured to form the projection data set by selecting two or more raw projections corresponding to a prescribed cardiac phase from a raw data set.

18. A CT cardiac image analysis system, comprising:
    means for segmenting a region of interest;
    means for selecting two or more successive projections from a projection data set, wherein each of the two or more successive projections are acquired at the same view angle and axial position and comprise a portion of data corresponding to a projection of the region of interest upon a detector;
    means for averaging the portion of data of each of the two or more successive projections to produce an averaged portion;
    means for replacing the portion of data of each of the two or more successive projections with the averaged portion to create two or more respective averaged projections;
    means for combining the two or more averaged projections with the remainder of the projection data set to produce a formatted data set; and
    means for reconstructing an image from the formatted data set.

19. The CT cardiac image analysis system as recited in claim 18, further comprising a means for interpolating a boundary region of data corresponding to data on at least one side of the portion of data within each of the two or more respective averaged projections.

20. A tangible medium comprising:
    a routine for segmenting a region of interest;
    a routine for selecting two or more successive projections from a projection data set, wherein each of the two or more successive projections are acquired at the same view angle and axial position and comprise a portion of data corresponding to a projection of the region of interest upon a detector;

a routine for averaging the portion of data of each of the two or more successive projections to produce an averaged portion;

a routine for replacing the portion of data of each of the two or more successive projections with the averaged portion to create two or more respective averaged projections;

a routine for combining the two or more averaged projections with the remainder of the projection data set to produce a formatted data set; and a routine for reconstructing an image from the formatted data set.

21. The tangible medium as recited in claim 20, wherein the routine for segmenting the region of interest accepts an operator input selecting the region of interest from a preliminary reconstructed image.

22. The tangible medium as recited in claim 20, wherein the routine for segmenting the region of interest includes an automated selection algorithm for selecting the region of interest from a preliminary reconstructed image.

23. The tangible medium as recited in claim 20, wherein the routine for segmenting the region of interest includes an automated selection algorithm for selecting the portion of data corresponding to the projection of the region of interest upon the detector from the processed data set.

24. The tangible medium as recited in claim 20, wherein the routine for segmenting the region of interest includes an automated selection algorithm for selecting the portion of data corresponding to the projection of the region of interest upon the detector from the projection data set.

25. The tangible medium as recited in claim 20, further comprising a routine for interpolating a boundary region of data corresponding to data on at least one side of the portion of data within each of the two or more respective averaged projections.

26. The tangible medium as recited in claim 25, wherein the routine for combining the two or more averaged projections with the remainder of the projection data set weights the remainder of the projection data set and the two or more averaged projections to compensate for redundancies.

27. The tangible medium as recited in claim 20, wherein the routine for combining the two or more averaged projections with the remainder of the projection data set weights the remainder of the projection data set and the two or more averaged projections to compensate for redundancies.

28. The tangible medium as recited in claim 20, further comprising a routine for selecting two or more raw projections corresponding to a prescribed cardiac phase from a raw data set to form the projection data set.

* * * * *